(12) United States Patent
Wu et al.

(10) Patent No.: US 7,658,551 B1
(45) Date of Patent: Feb. 9, 2010

(54) OPTICAL FIBER CONNECTOR

(75) Inventors: Chun-Hsiung Wu, Hsin-Tien (TW);
Chih-Min Wang, Hsin-Tien (TW);
Min-Chao Hsu, Hsin-Tien (TW); Jin Wu, Hsin-Tien (TW); Chia-Chu Lin, Hsin-Tien (TW)

(73) Assignee: Advanced Connectek Inc., Hsin-Tien, Taipei Hsien (TW)

( * ) Notice: Subject to any disclaimer, the term of this patent is extended or adjusted under 35 U.S.C. 154(b) by 0 days.

(21) Appl. No.: 12/353,794

(22) Filed: Jan. 14, 2009

(30) Foreign Application Priority Data

Oct. 27, 2008 (TW) .............................. 97219136 U

(51) Int. Cl.
*G02B 6/36* (2006.01)
(52) U.S. Cl. ......................................... 385/78; 385/84
(58) Field of Classification Search .............. 385/78–87
See application file for complete search history.

(56) References Cited

U.S. PATENT DOCUMENTS 6,206,581 B1 * 3/2001 Driscoll et al. ................. 385/78
6,293,710 B1   9/2001 Lampert et al.

* cited by examiner

*Primary Examiner*—Kevin S Wood
(74) *Attorney, Agent, or Firm*—patenttm.us

(57) ABSTRACT

An optical fiber connector has a rear housing, a reinforcing sleeve and a front housing. The rear housing has a front end, a rear end, a top, a bottom, two opposite sides and two slits longitudinally defined respectively through the top and the bottom at the front end. The reinforcing sleeve is mounted in the rear housing. The front housing is mounted around and the rear housing from the front end of the rear housing and completely covers the slits of the rear housing. The optical fiber connector with the slits has high resistance to the external transverse pulling force and is excellently durable.

7 Claims, 5 Drawing Sheets

OPTICAL FIBER CONNECTOR

BACKGROUND OF THE INVENTION

1. Field of the Invention

The present invention relates to a connector, and more particularly to an optical fiber connector that is structurally strong enough to have sufficient resistance to an external transverse pulling force without being damaged.

2. Description of Related Art

Optical fiber connectors are widely used in high-speed telecommunication devices to stably transmit light signals through optical fibers. One of general optical fiber connector is the Lucent connector (LC) designed by the Lucent Technologies.

Conventional Lucent connectors have a rear housing, a front housing and a ferrule. The rear housing is longitudinal and hollow and has a front open end and a through hole defined through the rear housing so that optical fibers of an optical cable are mounted through the through hole. The front housing is longitudinal and hollow and has a top, a bottom, a rear open end, a mounting hole and two slits. The mounting hole is defined through the front housing so that the optical fibers are mounted therethrough. The slits are defined respectively through the top and the bottom adjacent to the rear open end. With the slits, the rear open end would resiliently enlarge to allow the rear housing to extend easily into the front housing. The ferrule is mounted in the through hole and the mounting hole and is mounted securely around the optical fibers to position the optical fibers in the front and rear housings. However, when the optical cable on the Lucent connector suffers an external pulling force that is perpendicular to the Lucent connector with an included angle of about 90 degree between the external pulling force and the Lucent connector, the slits of the front housing are easily split.

With reference to FIG. 1, U.S. Pat. No. 6,293,710 discloses an improved Lucent connector (9) that comprises a front housing (91) and a rear housing (92). The front housing (91) has a top, a bottom, a rear open end and two slits (911). The rear housing (92) is mounted around the front housing (91) and has partially covers the slits (911) of the front housing (91). The rear housing (92) partially covering the slits (911) barely prevents the slits (911) from being split. However, the slits (911) are exposed partially. When an external pulling force is applied to the optical cable connected to the Lucent connector (9), the boundary between the covered parts and exposed parts of the slits (911) would be am initial portion being unable to endure the force and starting to split or wear. Therefore, the conventional Lucent connectors are not durable and have low resistance to pulling forces.

To overcome the shortcomings, the present invention provides an optical fiber connector to mitigate or obviate the aforementioned problems.

SUMMARY OF THE INVENTION

The main objective of the invention is to provide an optical fiber connector that is structurally strong enough to have sufficient resistance to an external transverse pulling force without being damaged.

An optical fiber connector in accordance with the present invention has a rear housing, a reinforcing sleeve and a front housing. The rear housing has a front end, a rear end, a top, a bottom, two opposite sides and two slits longitudinally defined respectively through the top and the bottom at the front end. The reinforcing sleeve is mounted in the rear housing. The front housing is mounted around and the rear housing from the front end of the rear housing and completely covers the slits of the rear housing. The optical fiber connector with the slits has high resistance to the external transverse pulling force and is excellently durable.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
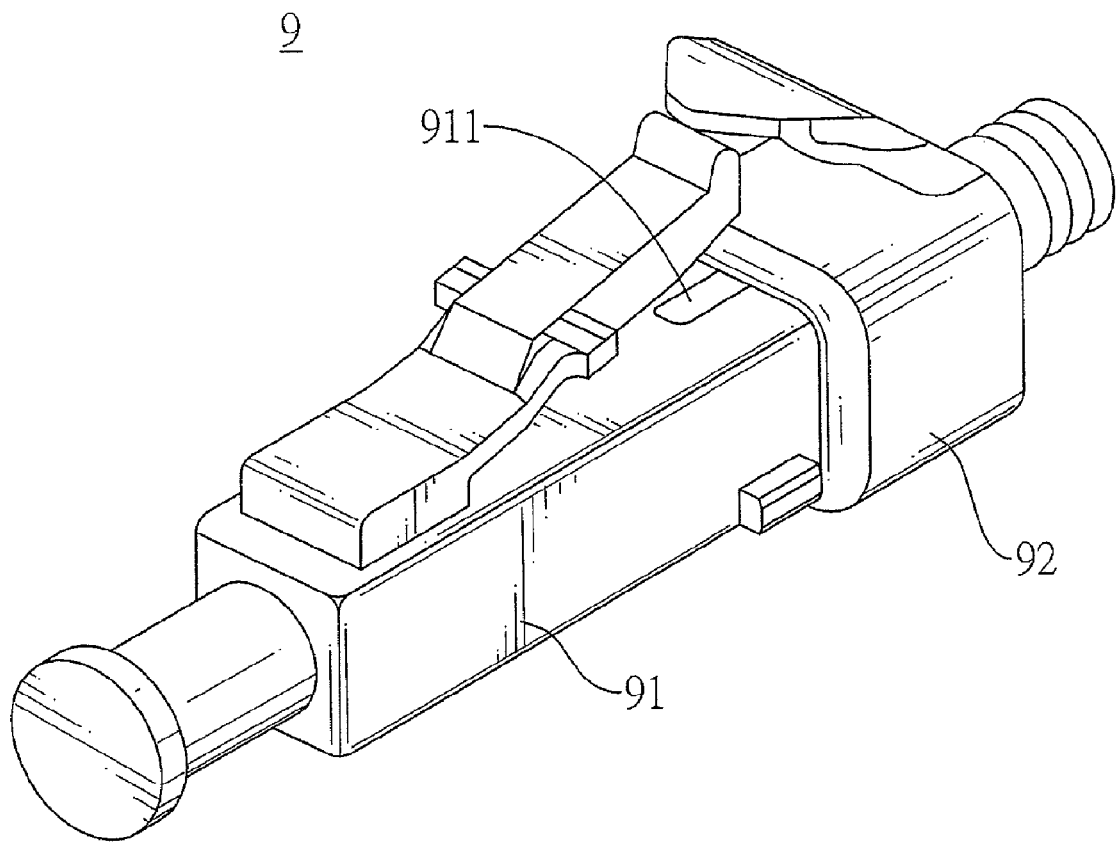
FIG. 1 is a perspective view of a conventional optical fiber connector in accordance with the prior art.
Figure 2:
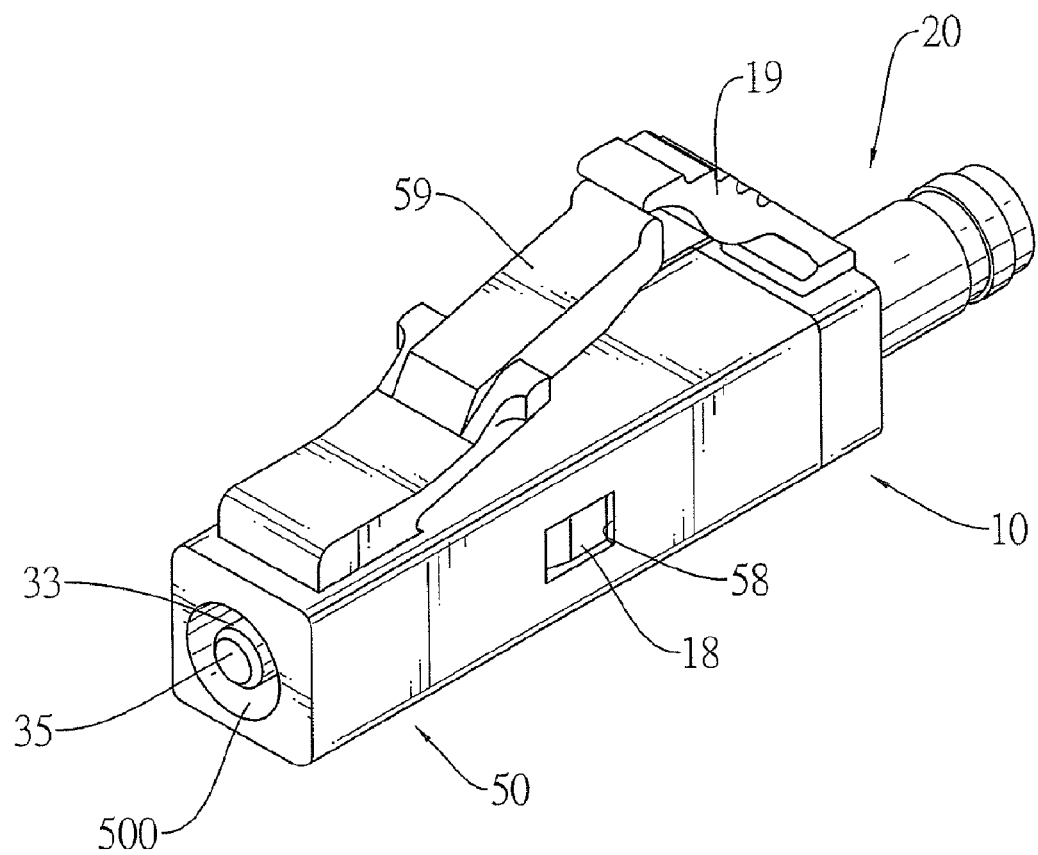
FIG. 2 is a perspective view of an optical fiber connector in accordance with the present invention.
Figure 3:
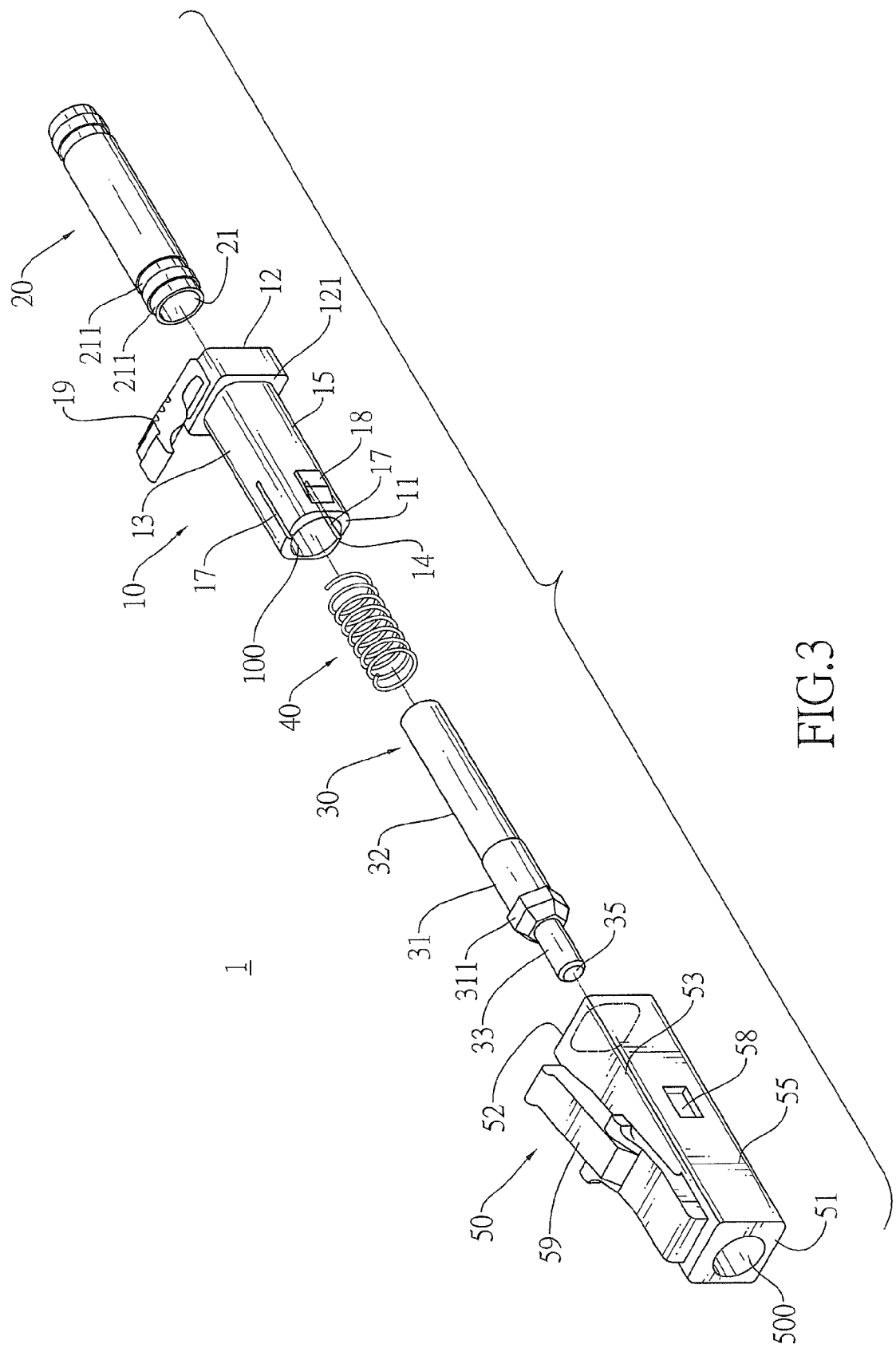
FIG. 3 is an exploded perspective view of the optical fiber connector in FIG. 2.
Figure 5:
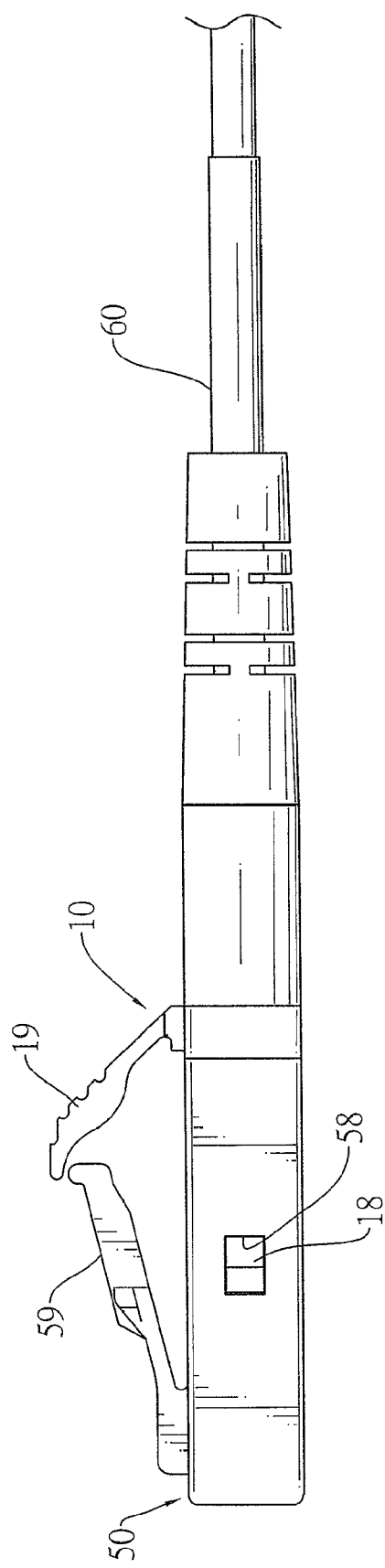
FIG. 5 is a side view of the optical fiber connector in FIG. 2 connected to an optical cable having optical fibers.

With reference to FIGS. 2, 3 and 5, an optical fiber connector (1) in accordance with the present invention may be compatible and comply with the Lucent (LC) connector designed by the Lucent Technologies and may be connected to an optical cable (60). The optical cable (60) has optical fibers.

The optical fiber connector (1) comprises a rear housing (10), a reinforcing sleeve (20), a front housing (50), a ferrule assembly (30) and a spring (40).

Figure 4:
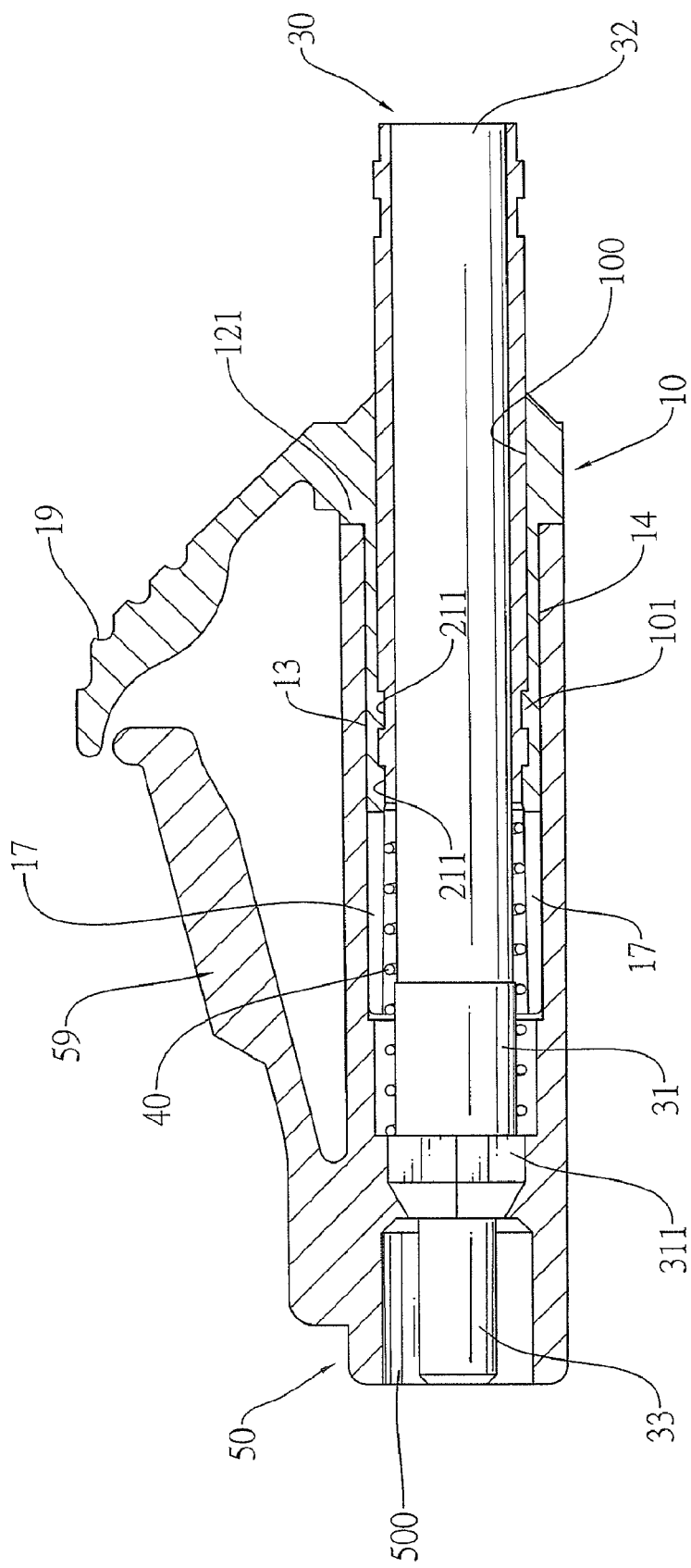
FIG. 4 is a side view in partial section of the optical fiber connector in FIG. 2.

With further reference to FIG. 4, the rear housing (10) is longitudinal and has a front end (11), a rear end (12), a top (13), a bottom (14), two opposite sides (15), a length, a through hole (100) and two slits (17) and may further have a stopper (121), two mounting hooks (18) and a releasing button (19).

The through hole (100) is defined longitudinally through the rear housing (10) from the front end (11) to the rear end (12), has an inner surface and may further have a plurality of ribs (101). The ribs (101) are annular and formed on the inner surface.

The slits (17) are longitudinally defined respectively through the top (13) and the bottom (14) at the front end (11) and each slit (17) has an front opening at the front end (11) and a length. The length of each slit (17) may be less than half the length of the rear housing (10). The slits (17) separate the rear housing (10) into opposite left and right halves that are resilient and compressible. The left and right halves may be compressed towards each other to reduction a diameter of the front end (11).

The stopper (121) is formed on and protrudes radially out from the rear end (12) of the rear housing (10).

The mounting hooks (18) are formed on and protrude respectively from the sides (15).

The releasing button (19) is resilient and longitudinal and is formed on and protrudes forwards and upwards from the stopper (121).

The reinforcing sleeve (20) is mounted in the through hole (100) of the rear housing (10) and extends partially out of the rear end (12), may be connected to the optical cable (60) and has a front end, a rear end, an outer surface and a fastening hole (21) and may further have a plurality of mounting grooves (211). The fastening hole (21) is defined longitudinally through the reinforcing sleeve (20) from the front end to the rear end. The mounting grooves are annular, are defined in the outer surface and are engaged respectively with the ribs (101) of the rear housing (10) to securely hold the reinforcing sleeve (20) in the rear housing (10).

The front housing (50) is longitudinal, is mounted around and covers the rear housing (10) from the front end (11) of the rear housing (10), may cover at least half the length of the rear housing (10) and completely covers the slits (17) of the rear housing (10). The front housing (50) has a fore end (51), a back end (52), a top (53), a bottom, two opposite sides (55) and a mounting hole (500) and may further have two fastening bores (58) and a socket fastener (59).

The back end (52) of the front housing (50) may abut against the stopper (121) of the rear housing (10).

The mounting hole (500) is defined longitudinally through the front housing (50) from the fore end (51) to the back end (52).

The fastening bores (58) are defined respectively through the sides (55), communicate with the mounting hole (500) and are engaged respectively with the fastening hooks (18) of the rear housing (10) to securely combine the front housing (50) and the rear housing (10).

The socket fastener (59) is resilient and longitudinal, is formed on and protrudes backwards and upwards from the fore end (51) of the front housing (50) and has a distal end located under and abutting against the releasing button (19) of the rear housing (10). When the optical fiber connector (1) is plugged in a corresponding socket, the socket fastener (59) hooks in the socket to prevent inadvertent disconnection between the optical fiber connector (1) and the socket. To detach the optical fiber connector (1) from the socket, the releasing button (121) is depressed to press the socket fastener (59) so that the socket fastener is unhooked from the socket and the optical fiber connector (1) is detached.

The ferrule assembly (30) is mounted in the fastening hole (21) of the reinforcing sleeve (20) and has a ferrule (31), a tube (32) and a head bushing (33).

The ferrule (31) is made of metal, is tubular, is mounted in the mounting hole (500) of the front housing (50) and has a front end, a rear end, a central hole and a nut (311). The central hole is defined through the ferrule (31). The nut (311) is formed on and protrudes radially from the front end of the ferrule (31) and may be polygonal such as hexagonal. People may easily hold the ferrule (31) by clamping the polygonal nut (311) and prevent inadvertent rotation or slip of the ferrule (31) when assembling optical fibers through the ferrule (31).

The tube (32) is mounted in the central hole through the rear end of the ferrule (31), extends in the fastening hole (21) through the front end of the reinforcing sleeve (20) and may accommodate the optical fibers of the optical cable (60).

The head bushing (33) is mounted in the front end of the ferrule (31) and has a mounting aperture (35) defined in the head bushing (33) to accommodate and hold the optical fibers of the optical cable (60).

The spring (40) is mounted in the mounting hole (500) of the front housing (50) and is mounted between the nut (311) of the ferrule (31) and the front end of the reinforcing sleeve (20) and has two ends. The ends of the spring (40) abut respectively against the nut (311) and the front end of the reinforcing sleeve (20) to bias the ferrule (31) and optical fibers forwards.

Because the front housing (50) almost covers the rear housing (10) entirely and completely covers the slits (17), the slits (17) would not expand excessively to inadvertently split the rear housing (10). When the optical cable (60) connected to the optical fiber connector (1) is pulled by an external transverse force substantially perpendicular to the optical fiber connector (1), the front housing (50) securely surrounds and holds the rear housing (10) to prevent over expansion of slits (17) to prevent any rupture of the rear housing (10) due to the external transverse force. Furthermore, the front housing (50) fully shield the slits (17) and the back end (52) of the front housing (50) would not overlap and intersect the slits (17). Therefore, the stress from the external transverse force would not act on the slits (17) so that the slits (17) would not easily deform or split. Thus, the optical fiber connector (1) with the slits (17) has high resistance to the external transverse pulling force and is excellently durable.

Even though numerous characteristics and advantages of the present invention have been set forth in the foregoing description, together with details of the structure and function of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An optical fiber connector comprising:
   a rear housing being longitudinal and having
      a front end, a rear end, a top, a bottom, two opposite sides and a length and further having
         a through hole defined longitudinally through the rear housing from the front end to the rear end and having an inner surface; and
         two slits longitudinally defined respectively through the top and the bottom at the front end and each slit having
            an front opening being at the front end; and
            a length;
   a reinforcing sleeve mounted in the through hole of the rear housing and extending partially out of the rear end and having a front end, a rear end, an outer surface and a fastening hole defined longitudinally through the reinforcing sleeve from the front end to the rear end; and
   a front housing being longitudinal, mounted around and covering the rear housing from the front end of the rear housing, completely covering the slits of the rear housing and having a fore end, a back end, a top, a bottom, two opposite sides and a mounting hole defined longitudinally through the front housing from the fore end to the back end.

2. The optical fiber connector as claimed in claim 1, wherein the front housing covers at least half the length of the rear housing.

3. The optical fiber connector as claimed in claim 2, wherein the length of each slit is be less than half the length of the rear housing.

4. The optical fiber connector as claimed in claim 3, wherein
   the rear housing further has a stopper formed on and protruding from the rear end of the rear housing; and
   the back end of the front housing abuts against the stopper of the rear housing.

5. The optical fiber connector as claimed in claim 4, wherein
   the rear housing further has a releasing button being resilient and formed on and protruding forwards and upwards from the stopper; and
   the front housing further has a socket fastener being resilient, formed on and protruding backwards and upwards from the fore end of the front housing and having a distal end located under and abutting against the releasing button of the rear housing.

6. The optical fiber connector as claimed in claim 5, wherein
- the rear housing further has a plurality of ribs being annular formed on the inner surface of the through hole; and
- the reinforcing sleeve further has a plurality of mounting grooves being annular, defined in the outer surface and engaged respectively with the ribs of the rear housing.

7. The optical fiber connector as claimed in claim 6 further comprising
- a ferrule assembly mounted in the fastening hole of the reinforcing sleeve and having
  - a ferrule being tubular, mounted in the mounting hole of the front housing and having a front end, a rear end and a nut formed on and protruding radially from the front end of the ferrule;
  - a tube mounted in the ferrule through the rear end of the ferrule and extending in the fastening hole through the front end of the reinforcing sleeve; and
  - a head bushing mounted in the front end of the ferrule; and
- a spring mounted in the mounting hole of the front housing and mounted between the nut of the ferrule and the front end of the reinforcing sleeve.

* * * * *